United States Patent
Zheng et al.

(10) Patent No.: US 12,420,008 B2
(45) Date of Patent: Sep. 23, 2025

(54) APPARATUS FOR AND METHOD IN DIRECT DRUG INFUSION USING A LABEL AS A HANGER

(71) Applicants: Genentech, Inc., South San Francisco, CA (US); Hoffmann-La Roche Inc., Little Falls, NJ (US)

(72) Inventors: Kai Zheng, Foster City, CA (US); Edward Porock, San Francisco, CA (US); Mahesh Khurana, San Bruno, CA (US); Geoffrey Colin Wise, San Jose, CA (US); Lorenzo Myles Paredes Pesino, San Francisco, CA (US); Michelle Hatch, San Antonio, TX (US); Stefan Yohe, San Francisco, CA (US); Raffaella Claudia Bondi, Basel (CH)

(73) Assignees: Genentech, Inc., South San Francisco, CA (US); Hoffmann-La Roche Inc., Little Falls, NJ (US)

( * ) Notice: Subject to any disclaimer, the term of this patent is extended or adjusted under 35 U.S.C. 154(b) by 161 days.

(21) Appl. No.: 17/795,506

(22) PCT Filed: Jan. 26, 2021

(86) PCT No.: PCT/US2021/015130
§ 371 (c)(1),
(2) Date: Jul. 26, 2022

(87) PCT Pub. No.: WO2021/154755
PCT Pub. Date: Aug. 5, 2021

(65) Prior Publication Data
US 2023/0095587 A1    Mar. 30, 2023

Related U.S. Application Data

(60) Provisional application No. 62/966,495, filed on Jan. 27, 2020.

(51) Int. Cl.
*A61M 5/14* (2006.01)
*A61J 1/14* (2023.01)
(Continued)

(52) U.S. Cl.
CPC .......... *A61M 5/1417* (2013.01); *A61J 1/1412* (2013.01); *A61M 5/142* (2013.01); *B65D 23/005* (2013.01); *A61M 2005/1402* (2013.01)

(58) Field of Classification Search
CPC .... B65D 23/005; A61M 5/1417; A61M 5/142
(Continued)

(56) References Cited

U.S. PATENT DOCUMENTS 1,971,528 A    8/1934  Leo
1,987,418 A    1/1935  Plishker et al.
(Continued)

FOREIGN PATENT DOCUMENTS

CN    102892459 A    1/2013
DE    102004046552 A1    4/2006
(Continued)

OTHER PUBLICATIONS (2001) Alburx (albumin-human solution), CSL Behring AG, 9 pages.
(Continued)

*Primary Examiner* — Stephen J Castellano
(74) *Attorney, Agent, or Firm* — Mintz Levin Cohn Ferris Glovsky and Popeo, P.C.

(57) ABSTRACT

An apparatus and method for direct drug infusion from a vial to a patient are provided. A movable hanger label is provided to adhere to and support the vial to facilitate direct infusion of a drug, such as one or more pharmaceuticals, biopharmaceuticals, and/or biologics, from the vial to the patient. Additionally, a process is provided in which the drug, contained in the vial with the movable hanger label, may be
(Continued)

directly infused through a primed infusion line with a rapid infusion rate. A saline flush is incorporated at the end of the administration to flush the infusion line, resulting in a reduced amount of the drug remaining in the line.

18 Claims, 8 Drawing Sheets

(51) Int. Cl.
*A61M 5/142* (2006.01)
*B65D 23/00* (2006.01)

(58) Field of Classification Search
USPC .................................................. 215/299, 399
See application file for complete search history.

(56) References Cited

U.S. PATENT DOCUMENTS

| | | | |
|---|---|---|---|
| 2,881,766 A | 4/1959 | Tornsjo | |
| 3,212,214 A | 10/1965 | Patterson | |
| 3,266,298 A | 8/1966 | Whitehead et al. | |
| 3,273,781 A | 9/1966 | Mills | |
| 3,744,658 A | 7/1973 | Fujio | |
| 4,048,737 A | 9/1977 | Mcdermott | |
| 4,306,662 A | 12/1981 | Sciortino et al. | |
| D275,177 S | 8/1984 | Villanueva | |
| 5,135,125 A | 8/1992 | Andel et al. | |
| 5,141,254 A | 8/1992 | Ring | |
| 5,490,658 A * | 2/1996 | Coward | B65D 23/005 248/205.3 |
| 5,732,491 A | 3/1998 | Burtch | |
| 5,738,381 A | 4/1998 | Treleaven et al. | |
| 5,782,495 A | 7/1998 | Grosskopf et al. | |
| 5,823,503 A | 10/1998 | Wasserman | |
| 5,829,788 A | 11/1998 | Jackson | |
| 5,878,901 A * | 3/1999 | Grosskopf | B32B 27/08 428/101 |
| 5,967,560 A | 10/1999 | Seidl | |
| 6,110,553 A | 8/2000 | Grosskopf et al. | |
| D443,894 S | 6/2001 | Schwartz | |
| 6,272,780 B1 | 8/2001 | Satamian | |
| 6,349,974 B1 | 2/2002 | Grosskopf et al. | |
| 6,457,747 B1 | 10/2002 | Treleaven et al. | |
| 6,546,656 B2 | 4/2003 | Twentier | |
| D585,944 S | 2/2009 | Lee | |
| D596,240 S | 7/2009 | Muniz et al. | |
| D613,451 S | 4/2010 | Welsh | |
| D676,490 S | 2/2013 | Bratter et al. | |
| D676,572 S | 2/2013 | Tarriff | |
| D702,765 S | 4/2014 | Williams | |
| D729,313 S | 5/2015 | Glass et al. | |
| D741,955 S | 10/2015 | Clark | |
| D752,682 S | 3/2016 | Sato et al. | |
| D785,710 S | 5/2017 | Lin | |
| D785,711 S | 5/2017 | Lin | |
| D786,976 S | 5/2017 | Keating | |
| D860,322 S | 9/2019 | Edwards | |
| D888,828 S | 6/2020 | Dittrich | |
| D892,212 S | 8/2020 | Sato et al. | |
| D927,596 S | 8/2021 | Monarque | |
| D931,370 S | 9/2021 | Khurana et al. | |
| D999,636 S | 9/2023 | Roses et al. | |
| 2002/0073587 A1 | 6/2002 | Twentier | |
| 2003/0004469 A1 | 1/2003 | Kraushaar | |
| 2004/0104274 A1 | 6/2004 | Kotik et al. | |
| 2004/0219331 A1 | 11/2004 | Moosheimer et al. | |
| 2007/0014958 A1 | 1/2007 | Chaplin et al. | |
| 2011/0004187 A1 * | 1/2011 | Beiriger | A61M 5/162 604/500 |
| 2013/0279832 A1 * | 10/2013 | Burri | B65D 75/5811 493/264 |
| 2015/0126959 A1 * | 5/2015 | Nakash | A61M 5/1407 604/153 |
| 2017/0053071 A1 * | 2/2017 | Caputo | G06K 7/10366 |
| 2018/0022522 A1 * | 1/2018 | Kannengiesser | B65D 71/066 206/497 |
| 2019/0294937 A1 | 9/2019 | Blair | |

FOREIGN PATENT DOCUMENTS

| | | |
|---|---|---|
| DE | 20201200754 U1 | 9/2012 |
| DE | 102012015557 A1 | 2/2014 |
| EP | 2695824 A1 | 2/2014 |
| JP | S60-144445 U | 9/1985 |
| JP | 2005218863 A | 8/2005 |
| JP | 2011516178 A | 5/2011 |
| TW | D129022 | 6/2009 |
| TW | D140218 S1 | 4/2011 |
| WO | 2021154755 A1 | 8/2021 |

OTHER PUBLICATIONS (2023) Intravenous Hanger Labels, cclhealthcare.com, 10 pages.
(Jan. 7, 2021) Albumin (Human) 25% Solution Albu Rx® 25, CSL Behring,, http://www.ffenterprises.com/assets/downloads/pi-AlbuminPPF ALBURX25CSLBehring.pdf>, 2 pages.
(Jan. 7, 2021) Alburx 25% 100ml CSL, Prescribing Details,, Available at: <https://biosupply.ffenterprises.com/alburx-25-100ml-csl-5.html#>, 3 pages.
(Jan. 7, 2021) NOC 44206-310 Alburx, Albumin (human) description,, Avilable at: https://ndclist.com/ndc/44206-310#description>, 7 pages.
Goldberg et al. (Dec. 18, 2017) "Mass General Hospital Raises Red Flag About National Shortage of IV Fluids", Available at: https://www.wbur.org/commonhealth/2017/12/18/mass-general-hospital-iv-fluids>, 7 pages.
International Search Report and Written Opinion received for Application No. PCT/US2021/015130 mailed on May 18, 2021, 15 pages.

* cited by examiner

APPARATUS FOR AND METHOD IN DIRECT DRUG INFUSION USING A LABEL AS A HANGER

CROSS-REFERENCE TO RELATED APPLICATIONS

This application is a National Stage Entry of International Patent Application No. PCT/US2021/015130, filed Jan. 26, 2021, and entitled, "Apparatus and Method in Direct Drug Infusion Using a Label as a Hanger," which claims priority to U.S. Provisional Application No. 62/966,495, filed on Jan. 27, 2020, the contents of each of which are herein incorporated by reference in its entirety.

TECHNICAL FIELD

The current subject matter described herein relates generally to drug infusion from a vial to a patient. More particularly, the current subject matter relates to an apparatus and a method that provides for direct drug infusion from a vial to a patient.

BACKGROUND

Infusion of a drug, such as one or more pharmaceuticals, biopharmaceuticals, and/or biologics, may involve an intravenous administration of the drug into the patient. One or more health care providers may be responsible for the intravenous administration, which may include, for example, dose preparation procedures and patient preparation procedures to provide for the drug to be intravenously administered to the patient.

SUMMARY

Aspects of the current subject matter relate to direct drug infusion from a vial to a patient, thereby simplifying the health care provider's workflow and reducing the infusion time for the patient.

This innovation simplifies the health care provider's workflow by allowing direct intravenous (IV) infusion of an undiluted liquid drug solution from its primary container. It does not require dilution into IV bags prior to administration and has a shorter infusion time. Therefore, it provides a more convenient and faster IV administration option for healthcare systems. Because it reduces the infusion time substantially, it is also expected to improve patient experience.

According to aspects disclosed herein, an apparatus is provided. The apparatus includes a label. The label includes a back surface area, and a front surface area opposite the back surface area. A portion of the back surface area of the label and an opposing portion of the front surface area of the label include a movable hanger. The movable hanger is configured to move from a first position to a second position. In the first position, the movable hanger is at least substantially aligned with a remainder portion of the back surface area and an opposing remainder portion of the front surface area. In the second position, the movable hanger is at least partially separated from the remainder portion of the back surface area and the opposing remainder portion of the front surface area.

In some variations, one or more of the features disclosed herein including the following features can optionally be included in any feasible combination. In some variations, the remainder portion of the back surface area of the label may be configured to adhere to an outer sidewall of a vial. In some variations, the label may include a flexible material. In some variations, the back surface area may include the portion of the back surface area and the remainder portion of the back surface area, and the front surface area may include the opposing portion of the front surface area and the opposing remainder portion of the front surface area. In some variations, the label may further include a perforation that extends through the back surface area and the front surface area, and the perforation may define at least a portion of a perimeter of the movable hanger. In some variations, the perforation may be configured to cause the movable hanger to at least partially separate from the remainder portion of the back surface area and the opposing remainder portion of the front surface area. In some variations, the movable hanger may be configured to move from the first position to the second position along the perforation. In some variations, the movable hanger in the second position may include a loop configuration, and the loop configuration may include two fixed ends. In some variations, the movable hanger in the second position may be configured to support a vial from an infusion stand, when the label is adhered to the vial. In some variations, the movable hanger in the second position may be positioned such that the vial hangs substantially downward away from the infusion stand. In some variations, the label may include text on the front surface area, and the text may be upside down, right side up, or a combination thereof when the vial hangs substantially downward. In some variations, the movable hanger in the second position may be configured to support a weight of the vial up to about 500 kg. In some variations, a length of the label may be between about 75 mm and about 100 mm. In some variations, a height of the label may be between about 30 mm and about 40 mm. In some variations, a width of the movable hanger may be between about 5 mm and about 7 mm.

In another, interrelated aspect, a method is provided. The method includes infusing, via an infusion pump, an infusion line with a first quantity of saline; removing a vial cap from a vial containing a drug, where the vial includes a stopper at a top portion thereof, and further where the vial cap is configured to cover the stopper; piercing the stopper with an infusion line spike at a proximal end of the infusion line; opening, from a label adhered to the vial, a movable hanger into a loop configuration, where the movable hanger is formed from a portion of the label and is configured to move from a closed configuration into the loop configuration; and hanging the vial, via the movable hanger, from an infusion stand.

In some variations, one or more of the features disclosed herein including the following features can optionally be included in any feasible combination. In some variations, the method may further include opening an air venting cap on the infusion line spike; and setting, on the infusion pump, an infusion rate and an infusion volume for the drug to be administered to a patient, such that the drug may travel from the vial, via the infusion line spike, through the infusion line to a needle inserted into the patient, where the needle may be positioned at a distal end of the infusion line, and further where the infusion pump may interface with the infusion line to pump the drug at the infusion rate. In some variations, the method may further include infusing, via the infusion pump and upon completion of administration of the drug to the patient, a second drug through the infusion line for administration to the patient, where the second drug may be of a same type or a different type as the drug. In some variations, the method may further include infusing, via the infusion pump, the infusion line with a second quantity of saline. In some variations, less than 1.5% of an initial volume of the drug may remain in the infusion line following the infusion of the second quantity of saline for an infusion time of up to about 30 minutes at an infusion rate of about 3 mL/min, where the infusion time may include a drug administration time and a second saline flush time. In some variations, less than 5% of an initial volume of the drug may remain in the infusion line following the infusion of the second quantity of saline for an infusion time of up to about 10 minutes at an infusion rate of about 6 mL/min, where the infusion time may include a drug administration time and a second saline flush time. In some variations, the drug may not be diluted prior to administration. In some variations, an initial amount of the drug in the vial may be less than about 30 mL. In some variations, the movable hanger may be formed from a portion of a back surface area and an opposing portion of a front surface area of the label. In some variations, the label may include a perforation that extends through the back surface area and the front surface area of the label, and the perforation may further define at least a portion of a perimeter of the movable hanger. In some variations, the perforation may be configured to cause the movable hanger to open into the loop configuration from the closed configuration.

In another, interrelated aspect, an apparatus is provided. The apparatus includes means for infusing an infusion line with a first quantity of saline; means for infusing the infusion line with a drug from a vial for administration of the drug to a patient; and means for infusing the infusion line with a second quantity of saline upon completion of the administration of the drug to the patient. The vial is suspended from an infusion stand via a movable hanger formed from a portion of a label adhered to the vial, where the movable hanger is configured to move from a closed configuration into a loop configuration.

In another, interrelated aspect, a method of administering a drug to a patient in need thereof is provided. The method includes infusing into the patient via an infusion line a first quantity of saline; infusing into the patient via the infusion line an infusion volume of the drug from a vial for a first period of time, where an initial amount of drug in the vial is less than or equal to about 30 mL and is not diluted prior to infusion into the patient; and infusing into the patient via the infusion line a second quantity of saline for a second period of time. Less than about 5% of the initial amount of the drug remains in the infusion line after infusion of the second quantity of saline.

In some variations, one or more of the features disclosed herein including the following features can optionally be included in any feasible combination. In some variations, the drug may be administered at a fixed dose. In some variations, the initial amount of drug in the vial may be less than or equal to about 10 mL. In some variations, the total of the first period of time and the second period of time may be less than or equal to about 60 minutes. In some variations, the total of the first period of time and the second period of time may be less than or equal to about 30 minutes. In some variations, the total of the first period of time and the second period of time may be less than or equal to about 15 minutes. In some variations, less than about 1.5% of the initial amount of the drug may remain in the infusion line after infusion of the second quantity of saline. In some variations, the infusion volume of the drug may be between about 10 mL and about 30 mL and the second quantity of saline may be between about 25 mL and about 90 mL. In some variations, the drug and second quantity of saline may be infused into the patient at an infusion rate between about 1 mL/min and about 10 mL/min.

The details of one or more variations of the subject matter described herein are set forth in the accompanying drawings and the description below. Other features and advantages of the subject matter described herein will be apparent from the description and drawings, and from the claims.

DESCRIPTION OF DRAWINGS

The accompanying drawings, which are incorporated in and constitute a part of this specification, show certain aspects of the subject matter disclosed herein and, together with the description, help explain some of the principles associated with the disclosed implementations. In the drawings.

When practical, similar reference numbers denote similar structures, features, or elements.

DETAILED DESCRIPTION

I. Definitions

Figure 1A:
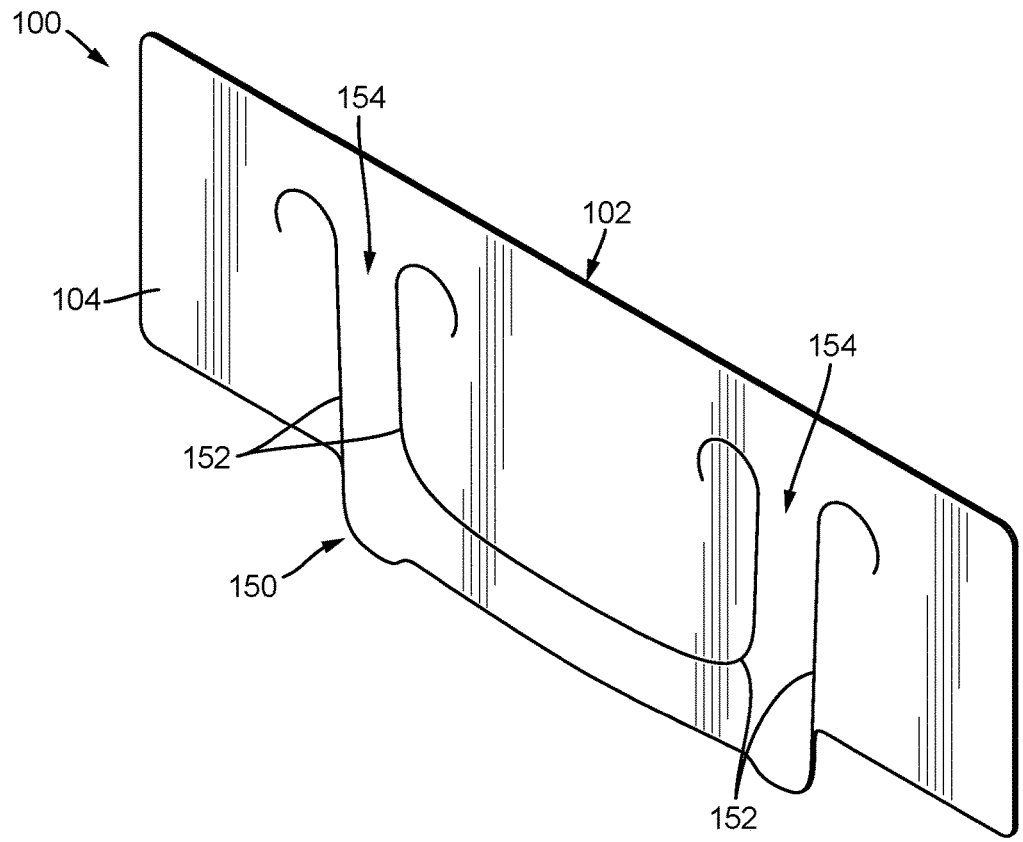
FIG. 1A, FIG. 1B, FIG. 2A, and FIG. 2B illustrate features of a movable hanger label configured to adhere to and support a vial consistent with implementations of the current subject matter.
Figure 1B:
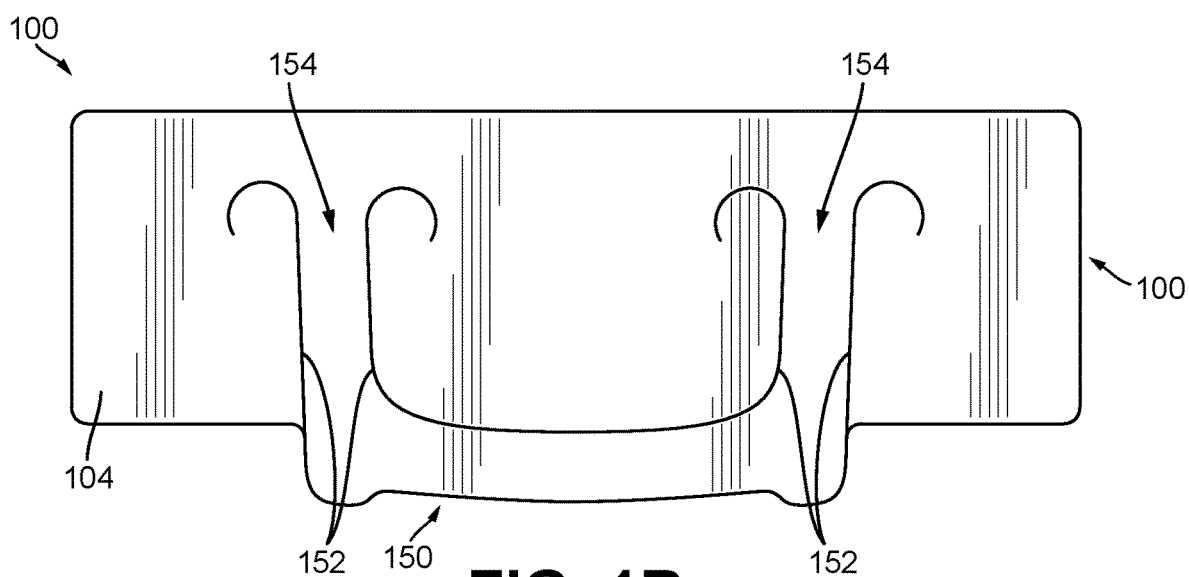

"Patient" or "subject in need thereof" refers to a living organism suffering from or prone to a disease or condition that can be treated by administration of a pharmaceutical composition as provided herein. Non-limiting examples include humans, other mammals, bovines, rats, mice, dogs, cats, monkeys, goat, sheep, cows, deer, and other non-mammalian animals. In some embodiments, a patient is human.

Dosages may be varied depending upon the requirements of the patient and the compound being employed. The dose administered to a patient, in the context of the present disclosure, should be sufficient to effect a beneficial therapeutic response in the patient over time. The size of the dose also will be determined by the existence, nature, and extent of any adverse side-effects. Determination of the proper dosage for a particular situation is within the skill of the practitioner. Dosage amounts and intervals can be adjusted individually to provide levels of the administered compound effective for the particular clinical indication being treated. This will provide a therapeutic regimen that is commensurate with the severity of the individual's disease state.

II. Pharmaceutical Compositions

An "anticancer agent" as used herein refers to a molecule (e.g. compound, peptide, protein, nucleic acid) used to treat cancer through destruction or inhibition of cancer cells or tissues. Anticancer agents may be selective for certain cancers or certain tissues. In embodiments, anticancer agents herein may include epigenetic inhibitors and multi-kinase inhibitors.

"Anti-cancer agent" and "anticancer agent" are used in accordance with their plain ordinary meaning and refers to a composition (e.g. compound, drug, antagonist, inhibitor, modulator) having antineoplastic properties or the ability to inhibit the growth or proliferation of cells. In some embodiments, an anti-cancer agent is a chemotherapeutic. In some embodiments, an anti-cancer agent is a biologic. In some embodiments, an anti-cancer agent is an immunotherapy agent. In some embodiments, an anti-cancer agent is an immune checkpoint inhibitor. In some embodiments, an anti-cancer agent is an agent identified herein having utility in methods of treating cancer. In some embodiments, an anti-cancer agent is an agent approved by the FDA or similar regulatory agency of a country other than the USA, for treating cancer. Examples of anti-cancer agents include, but are not limited to, MEK (e.g. MEK1, MEK2, or MEK1 and MEK2) inhibitors (e.g. XL518, CI-1040, PD035901, selumetinib/AZD6244, GSK1120212/trametinib, GDC-0973, ARRY-162, ARRY-300, AZD8330, PD0325901, U0126, PD98059, TAK-733, PD318088, AS703026, BAY 869766), alkylating agents (e.g., cyclophosphamide, ifosfamide, chlorambucil, busulfan, melphalan, mechlorethamine, uramustine, thiotepa, nitrosoureas, nitrogen mustards (e.g., mechloroethamine, cyclophosphamide, chlorambucil, meiphalan), ethylenimine and methylmelamines (e.g., hexamethlymelamine, thiotepa), alkyl sulfonates (e.g., busulfan), nitrosoureas (e.g., carmustine, lomusitne, semustine, streptozocin), triazenes (decarbazine)), anti-metabolites (e.g., 5-azathioprine, leucovorin, capecitabine, fludarabine, gemcitabine, pemetrexed, raltitrexed, folic acid analog (e.g., methotrexate), or pyrimidine analogs (e.g., fluorouracil, floxouridine, Cytarabine), purine analogs (e.g., mercaptopurine, thioguanine, pentostatin), etc.), plant alkaloids (e.g., vincristine, vinblastine, vinorelbine, vindesine, podophyllotoxin, paclitaxel, docetaxel, etc.), topoisomerase inhibitors (e.g., irinotecan, topotecan, amsacrine, etoposide (VP16), etoposide phosphate, teniposide, etc.), antitumor antibiotics (e.g., doxorubicin, adriamycin, daunorubicin, epirubicin, actinomycin, bleomycin, mitomycin, mitoxantrone, plicamycin, etc.), platinum-based compounds (e.g. cisplatin, oxaloplatin, carboplatin), anthracenedione (e.g., mitoxantrone), substituted urea (e.g., hydroxyurea), methyl hydrazine derivative (e.g., procarbazine), adrenocortical suppressant (e.g., mitotane, aminoglutethimide), epipodophyllotoxins (e.g., etoposide), antibiotics (e.g., daunorubicin, doxorubicin, bleomycin), enzymes (e.g., L-asparaginase), inhibitors of mitogen-activated protein kinase signaling (e.g. U0126, PD98059, PD184352, PD0325901, ARRY-142886, SB239063, SP600125, BAY 43-9006, wortmannin, or LY294002, Syk inhibitors, mTOR inhibitors, antibodies (e.g., rituxan), gossyphol, genasense, polyphenol E, Chlorofusin, all trans-retinoic acid (ATRA), bryostatin, tumor necrosis factor-related apoptosis-inducing ligand (TRAIL), 5-aza-2'-deoxycytidine, all trans retinoic acid, doxorubicin, vincristine, etoposide, gemcitabine, imatinib (Gleevec®), geldanamycin, 17-N-Allylamino-17-Demethoxygeldanamycin (17-AAG), flavopiridol, LY294002, bortezomib, trastuzumab, BAY 11-7082, PKC412, PD184352, 20-epi-1, 25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; 9-dioxamycin; diphenyl spiromustine; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides;

insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylerie conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen-binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; zinostatin stimalamer, Adriamycin, Dactinomycin, Bleomycin, Vinblastine, Cisplatin, acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cladribine; crisnatol mesylate; cyclophosphamide; cytarabine; dacarbazine; daunorubicin hydrochloride; decitabine; dexormaplatin; dezaguanine; dezaguanine mesylate; diaziquone; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; hydroxyurea; idarubicin hydrochloride; ifosfamide; iimofosine; interleukin Il (including recombinant interleukin II, or rIL.sub.2), interferon alfa-2a; interferon alfa-2b; interferon alfa-n1; interferon alfa-n3; interferon beta-1a; interferon gamma-1b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazoie; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride, agents that arrest cells in the G2-M phases and/or modulate the formation or stability of microtubules, (e.g. Taxol™ (i.e. paclitaxel), Taxotere™, compounds comprising the taxane skeleton, Erbulozole (i.e. R-55104), Dolastatin 10 (i.e. DLS-10 and NSC-376128), Mivobulin isethionate (i.e. as CI-980), Vincristine, NSC-639829, Discodermolide (i.e. as NVP-XX-A-296), ABT-751 (Abbott, i.e. E-7010), Altorhyrtins (e.g. Altorhyrtin A and Altorhyrtin C), Spongistatins (e.g. Spongistatin 1, Spongistatin 2, Spongistatin 3, Spongistatin 4, Spongistatin 5, Spongistatin 6, Spongistatin 7, Spongistatin 8, and Spongistatin 9), Cemadotin hydrochloride (i.e. LU-103793 and NSC-D-669356), Epothilones (e.g. Epothilone A, Epothilone B, Epothilone C (i.e. desoxyepothilone A or dEpoA), Epothilone D (i.e. KOS-862, dEpoB, and desoxyepothilone B), Epothilone E, Epothilone F, Epothilone B N-oxide, Epothilone A N-oxide, 16-aza-epothilone B, 21-aminoepothilone B (i.e. BMS-310705), 21-hydroxyepothilone D (i.e. Desoxyepothilone F and dEpoF), 26-fluoroepothilone, Auristatin PE (i.e. NSC-654663), Soblidotin (i.e. TZT-1027), LS-4559-P (Pharmacia, i.e. LS-4577), LS-4578 (Pharmacia, i.e. LS-477-P), LS-4477 (Pharmacia), LS-4559 (Pharmacia), RPR-112378 (Aventis), Vincristine sulfate, DZ-3358 (Daiichi), FR-182877 (Fujisawa, i.e. WS-9885B), GS-164 (Takeda), GS-198 (Takeda), KAR-2 (Hungarian Academy of Sciences), BSF-223651 (BASF, i.e. ILX-651 and LU-223651), SAH-49960 (Lilly/Novartis), SDZ-268970 (Lilly/Novartis), AM-97 (Armad/Kyowa Hakko), AM-132 (Armad), AM-138 (Armad/Kyowa Hakko), IDN-5005 (Indena), Cryptophycin 52 (i.e. LY-355703), AC-7739 (Ajinomoto, i.e. AVE-8063A and CS-39.HCl), AC-7700 (Ajinomoto, i.e. AVE-8062, AVE-8062A, CS-39-L-Ser.HCl, and RPR-258062A), Vitilevuamide, Tubulysin A, Canadensol, Centaureidin (i.e. NSC-106969), T-138067 (Tularik, i.e. T-67, TL-138067 and TI-138067), COBRA-1 (Parker Hughes Institute, i.e. DDE-261 and WHI-261), H10 (Kansas State University), H16 (Kansas State University), Oncocidin A1 (i.e. BTO-956 and DIME), DDE-313 (Parker Hughes Institute), Fijianolide B, Laulimalide, SPA-2 (Parker Hughes Institute), SPA-1 (Parker Hughes Institute, i.e. SPIKET-P), 3-IAABU (Cytoskeleton/Mt. Sinai School of Medicine, i.e. MF-569), Narcosine (also known as NSC-5366), Nascapine, D-24851 (Asta Medica), A-105972 (Abbott), Hemiasterlin, 3-BAABU (Cytoskeleton/Mt. Sinai School of Medicine, i.e. MF-191), TMPN (Arizona State University), Vanadocene acetylacetonate, T-138026 (Tularik), Monsatrol, lnanocine (i.e. NSC-698666), 3-IAABE (Cytoskeleton/Mt. Sinai School of Medicine), A-204197 (Abbott), T-607 (Tuiarik, i.e. T-900607), RPR-115781 (Aventis), Eleutherobins (such as Desmethyleleutherobin, Desaetyleleutherobin, lso-eleutherobin A, and Z-Eleutherobin), Caribaeoside, Caribaeolin, Halichondrin B, D-64131 (Asta Medica), D-68144 (Asta Medica), Diazonamide A, A-293620 (Abbott), NPI-2350 (Nereus), Taccalonolide A, TUB-245 (Aventis), A-259754 (Abbott), Diozostatin, (−)-Phenylahistin (i.e. NSCL-96F037), D-68838 (Asta Medica), D-68836 (Asta Medica), Myoseverin B, D-43411 (Zentaris, i.e. D-81862), A-289099 (Abbott), A-318315 (Abbott), HTI-286 (i.e. SPA-110, trifluoroacetate salt) (Wyeth), D-82317 (Zentaris), D-82318 (Zentaris), SC-12983 (NCI), Resverastatin phosphate sodium, BPR-OY-007 (National Health Research Institutes), and SSR-250411 (Sanofi)), steroids (e.g., dexamethasone), finasteride, aromatase inhibitors, gonadotropin-releasing hormone agonists (GnRH) such as goserelin or leuprolide, adrenocorticosteroids (e.g., prednisone), progestins (e.g., hydroxyprogesterone caproate, megestrol acetate, medroxyprogesterone acetate), estrogens (e.g., diethylstilbestrol, ethinyl estradiol), antiestrogen (e.g., tamoxifen), androgens (e.g., testosterone propionate, fluoxymesterone), antiandrogen (e.g., flutamide), immunostimulants (e.g., *Bacillus* Calmette-Guérin (BCG), levamisole, interleukin-2, alpha-interferon, etc.), monoclonal antibodies (e.g., anti-CD20, anti-HER2, anti-CD52, anti-HLA-DR, and anti-VEGF monoclonal antibodies), immunotoxins (e.g., anti-CD33 monoclonal antibody-calicheamicin conjugate, anti-CD22 monoclonal antibody-pseudomonas exotoxin conjugate, etc.), radioimmunotherapy (e.g., anti-CD20 monoclonal antibody conjugated to $^{111}$In, $^{90}$Y, or $^{131}$I, etc.), triptolide, homoharringtonine, dactinomycin, doxorubicin, epirubicin, topotecan, itraconazole, vindesine, cerivastatin, vincristine, deoxyadenosine, sertraline, pitavastatin, irinotecan, clofazimine, 5-nonyloxytryptamine, vemurafenib, dabrafenib, erlotinib, gefitinib, EGFR inhibitors, epidermal growth factor receptor (EGFR)-targeted therapy or therapeutic (e.g. gefitinib (Iressa™) erlotinib (Tarceva™), cetuximab (Erbitux™), lapatinib (Tykerb™), panitumumab (Vectibix™), vandetanib (Caprelsa™), afatinib/BIBW2992, CI-1033/canertinib, neratinib/HKI-272, CP-724714, TAK-285, AST-1306, ARRY334543, ARRY-380, AG-1478, dacomitinib/PF299804, OSI-420/desmethyl erlotinib, AZD8931, AEE788, pelitinib/EKB-569, CUDC-101, WZ8040, WZ4002, WZ3146, AG-490, XL647, PD153035, BMS-599626), sorafenib, imatinib, sunitinib, dasatinib, or the like. In an embodiment, the anti-cancer agent is an immune checkpoint inhibitor (e.g., atezolizumab (Tecentriq®), pembrolizumab (Keytruda®), Ipilimumab, Nivolumab (Opdivo®), Avelumab, Durvalumab, Cemiplimab, or spartalizumab).

III. Methods of Use

As used herein, the term "administering" generally means intravenous administration, unless otherwise indicated. Other modes of administration include, without limitation: administration as a suppository, topical contact, oral, parenteral, intraperitoneal, intramuscular, intralesional, intrathecal, intranasal, subcutaneous administration, implantation of a slow-release device, e.g., a mini-osmotic pump, transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, transdermal patches, etc.

It is understood that the examples and embodiments described herein are for illustrative purposes only and that various modifications or changes in light thereof will be suggested to persons skilled in the art and are to be included within the spirit and purview of this application and scope of the appended claims.

IV. Description

The current subject matter is directed to direct drug infusion from a vial to a patient. Consistent with implementations of the current subject matter, a movable hanger label is provided to adhere to and support the vial to facilitate direct infusion of a drug, such as one or more pharmaceuticals, biopharmaceuticals, and/or biologics, from the vial to the patient.

For a conventional drug infusion procedure, one or more health care providers may be responsible for the intravenous administration, which may include, for example, dose preparation procedures and patient preparation procedures to provide for the drug to be intravenously directed to the patient. For example, the dose preparation procedures may involve one or more health care providers preparing a diluted drug in an intravenous bag, which expends valuable resources of time (e.g., the time of the health care providers to prepare the diluted drug) and materials (e.g., the intravenous bag). Moreover, the dose preparation procedures need to be conducted in a sterile environment, further expending resources including sterile equipment (e.g., health care provider gloves and masks) and hospital or clinical space. Additionally, such dose preparation procedures inherently are at risk for error due to the reliance on human interaction in the preparation of the diluted drug.

With respect to patient considerations, conventional drug infusion procedures typically involve a significant amount of time to administer the drug to the patient. As the drug is diluted with, for example, saline, an increased amount of fluids are being delivered to the patient, thereby resulting in an increased amount of time for the drug administration.

The movable hanger label consistent with implementations of the current subject matter simplifies the conventional drug infusion procedure by providing for the drug to be directly infused to the patient from the vial. This decreases the time, material, and space resources that are involved in conventional dose preparation procedures. Additionally, use of the movable hanger label for the direct drug infusion of the drug to the patient reduces the amount of time for the drug administration, thereby increasing the overall patient experience.

Figure 2A:
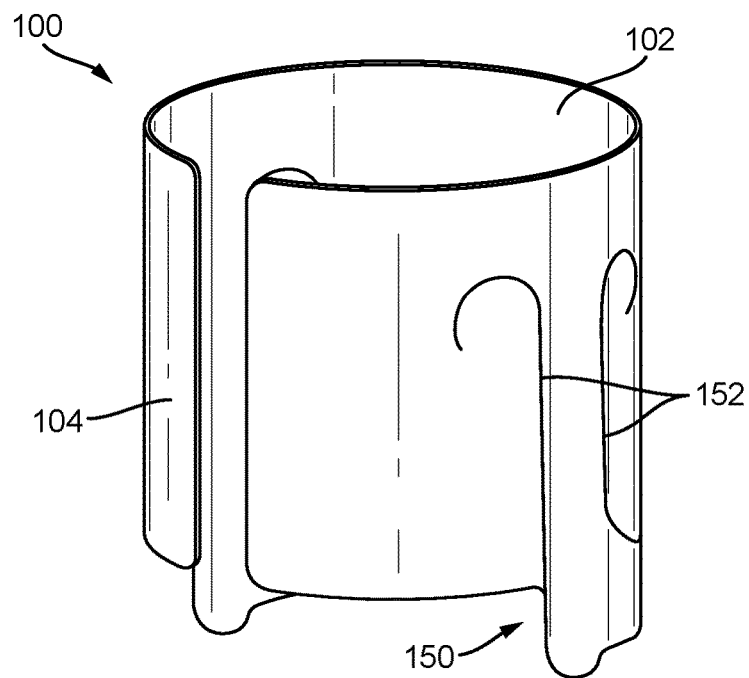
Figure 2B:
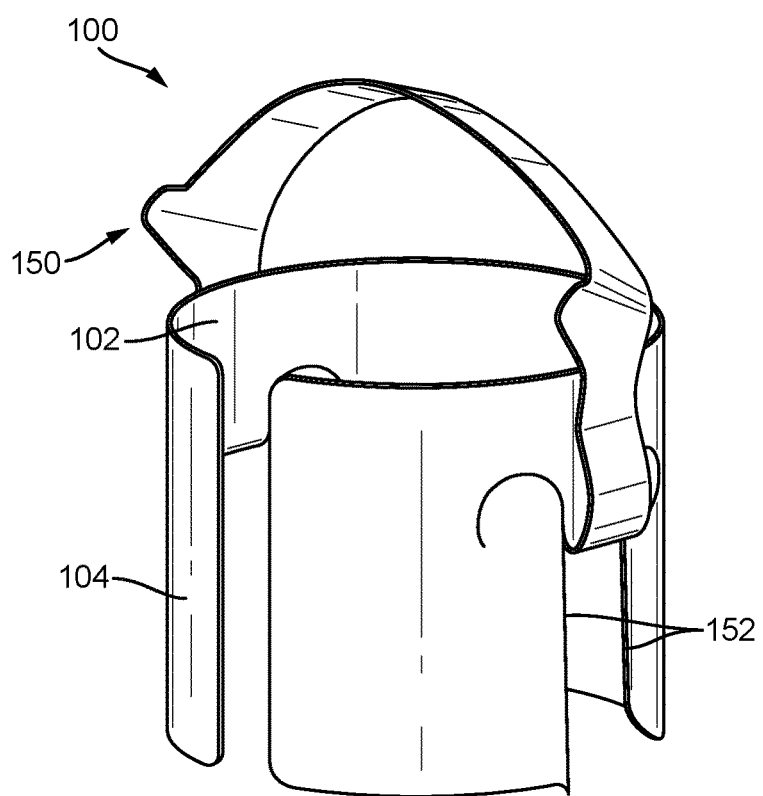

FIG. 1A-FIG. 2B illustrate features of a movable hanger label 100 configured to adhere to and support a vial consistent with implementations of the current subject matter. FIG. 1A is a perspective view of the movable hanger label 100 in a flat orientation, and FIG. 1B is a front view of the movable hanger label 100 in the flat orientation. FIG. 2A is a perspective view of the movable hanger label 100 in a curved orientation (e.g., a configuration in which the movable hanger label 100 is applied to a vial), and FIG. 2B is a perspective view of the movable hanger label 100 in a curved orientation with a movable hanger portion 150 in an open or loop configuration.

As shown in FIG. 1A-FIG. 2B, the movable hanger label 100 has a back surface area 102 and a front surface area 104 that is opposite the back surface area 102. The back surface area 102 and the front surface area 104 are generally planar surfaces. The movable hanger portion 150 is formed from a portion of the back surface area 102 and an opposing portion of the front surface area 104 of the movable hanger label 100, and is configured to move from a first position (e.g., a closed position or a closed configuration) to a second position (e.g., an open position or an open configuration or a loop position or a loop configuration). In the first position (e.g., the closed position), the movable hanger portion 150 is aligned with a remaining area of the movable hanger label 100. In the second position (e.g., the open position or the loop position), the movable hanger portion 150 of the movable hanger label 100 is at least partially separated from the remaining area of the movable hanger label 100. That is, consistent with implementations of the current subject matter, the movable hanger portion 150 is a portion of the movable hanger label 100 that may be moved relative to the movable hanger label 100 to form a loop or hanger 150 (as shown in FIG. 2B).

Consistent with implementations of the current subject matter, the movable hanger label 100 is perforated such that the movable hanger portion 150 is formed from a portion of the back surface area 102 and an opposing portion of the front surface area 104 of the movable hanger label 100. Perforations 152 allow for the movable hanger portion 150 to be at least partially separated from the remaining portion of the movable hanger label 100 so that the movable hanger portion 150 may move (along the perforations 152) relative to the movable hanger label 100, as shown in FIG. 2B. The perforations 152 define at least a portion of a perimeter of the movable hanger portion 150, as shown in FIG. 2B. The movable hanger portion 150 may be peeled away from the remaining portion of the movable hanger label 100 by grasping a first and/or second extended tab or corner or an end region of the movable hanger portion 150, and peeling the movable hanger portion 150 along the perforations 152.

The movable hanger portion 150 is fixed to the movable hanger label 100 at fixed ends 154 of the movable hanger label 100. The perforations 152 adjacent or near the fixed ends 154 may be in a curved form or the like to provide for or facilitate movement (e.g., rotational movement) of the movable hanger portion 150. The curved form of the end regions of the perforations 152 may also prevent the movable hanger label 100 from tearing at the end regions. For example, the movable hanger portion 150 may rotate from the closed position to the open position or the loop position by about 180°, and the curved form of the end regions of the perforations 152 provides for the rotation with no or minimal tearing of the movable hanger label 100 apart from the perforations 152.

The movable hanger label 100 consistent with implementations of the current subject matter is made of a flexible material such that the movable hanger label 100 is able to conform to the shape of a surface on which the movable hanger label 100 is being applied. For example, the movable hanger label 100 may be made of a flexible plastic or reinforced paper product. The movable hanger label 100 may adhere to a vial having a curved outer sidewall, and the movable hanger label 100 may substantially conform to the curvature of the outer sidewall of the vial. The movable hanger label 100 may conform to a variety of surface shapes and is not limited to being adhered to and used with a cylindrical vial but may also be used with, for example, a cubic vial.

The back surface area 102 of the movable hanger label 100 may include a bonding material or substance that sticks or adheres to a variety of materials, such as glass, plastic, metal, and the like. Consistent with implementations of the current subject matter, the portion of the back surface area 102 that forms the movable hanger portion 150 does not contain the bonding material or substance, allowing the movable hanger portion 150 to separate from the remainder of the movable hanger label 100 to move between the first position (e.g., the closed position) to the second position (e.g., the open or loop position) when the movable hanger label 100 is adhered to a vial.

Figure 3A:
FIG. 3A and FIG. 3B illustrate aspects of a movable hanger label adhered to a vial consistent with implementations of the current subject matter.
Figure 3B:
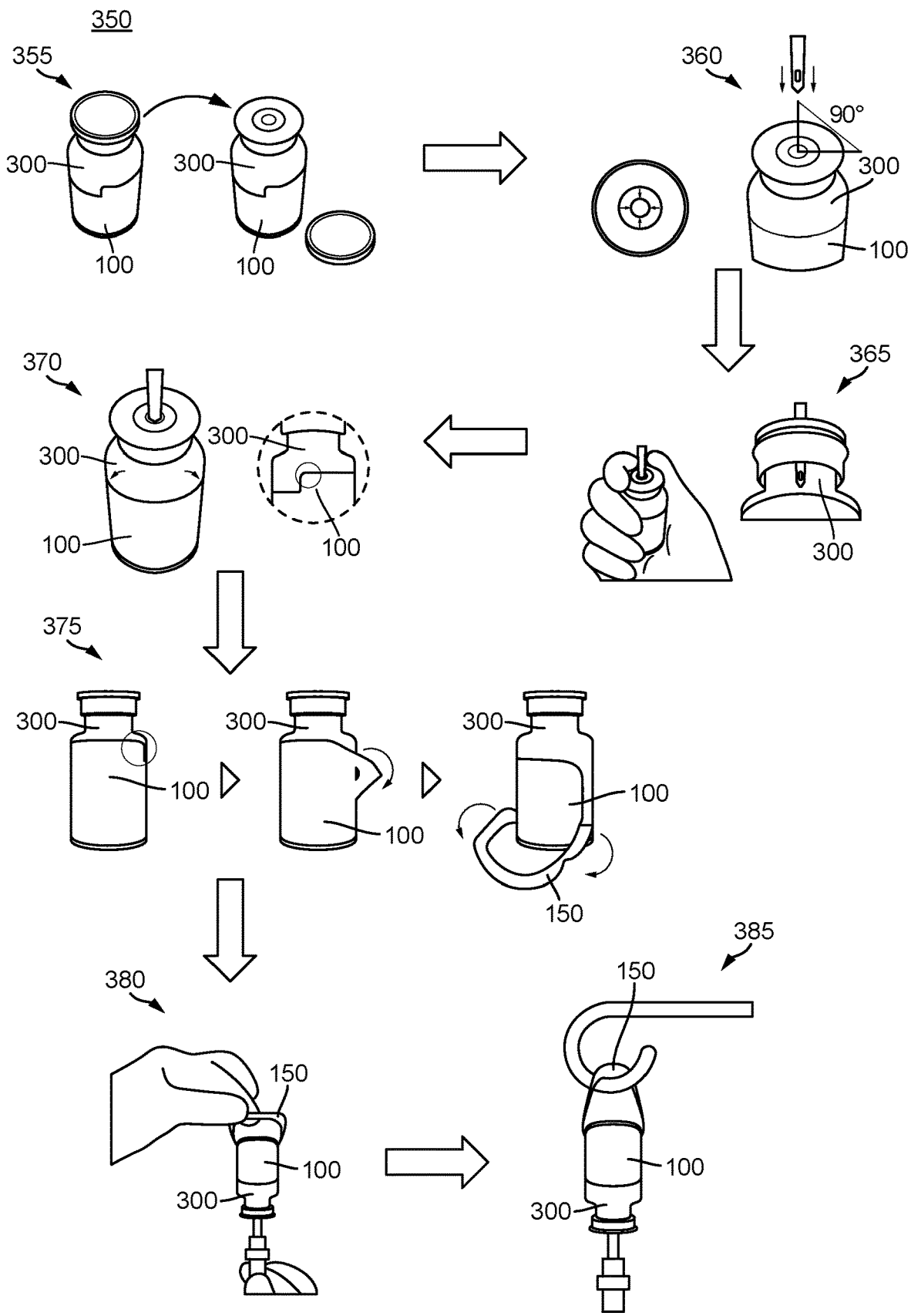

With reference to FIG. 3A-FIG. 3B, aspects of the movable hanger label 100 when adhered to a vial 300 consistent with implementations of the current subject matter are illustrated. On the left-hand side of FIG. 3A, the movable hanger label 100 is shown adhered to the vial 300 with the movable hanger portion 150 in the closed configuration (or position). On the right-hand side of FIG. 3A, the movable hanger portion 150 is moved from the closed configuration (or position) to the open configuration (or position), in which a type of hanger is formed as a result of the separation and movement (e.g., rotational movement) of the movable hanger portion 150 away from the remainder of the movable hanger label 100. As shown, the movable hanger portion 150 may take the form of a loop such that when the vial 300 is turned topside down, the loop (positioned at the bottom of the vial 300) is topside up, allowing the vial 300 to be attached or secured to an apparatus with the topside of the vial 300 accessible. Such configuration, as shown in FIG. 3B, provides for the drug contained in the vial 300 to be able to be directly accessed from the vial 300 while the vial is attached or secured (e.g., hanging from) an apparatus. For example, with the movable hanger portion 150 in the open configuration, the vial 300 may be secured to an infusion stand or the like by the movable hanger portion 150 being looped or otherwise secured to an arm or extension of the infusion stand or the like. In this configuration with the vial 300 supported by the movable hanger portion 150 of the movable hanger label 100 and with the vial 300 oriented substantially downward, text and/or markings on the movable hanger label 100 may be upside down, right side up, or a combination thereof. For example, consistent with implementations of the current subject matter, text and/or markings on the movable hanger label 100 may be upside down when the vial 300 is situated in an upright position, allowing for the text and/or markings to be right side up when the vial 300 is hanging and supported by the movable hanger portion 150.

With further reference to FIG. 3B, a process 350 of preparing the vial 300 with the movable hanger label 100 for drug administration to a patient of a drug contained in the vial 300 is shown.

At 355, a vial cap is removed from the vial 300 containing the drug. As shown, the movable hanger label 100 is adhered to the vial 300. In some examples, the vial 300 may include a stopper at a top portion thereof, and the vial cap may be configured to cover the stopper.

At 360, the vial stopper is pierced with an infusion line spike, which interfaces with an infusion line (not shown in FIG. 3B). In some examples, the infusion line spike pierces a center or near center portion of the vial stopper. In some examples, a lengthwise orientation of the infusion line spike is 90° with respect to a top surface of the vial stopper. In some examples, the lengthwise orientation of the infusion line spike is about 80°, about 81°, about 82°, about 83°, about 84°, about 85°, about 86°, about 87°, about 88°, about 89°, about 90°, about 91°, about 92°, about 93°, about 94°, about 95°, about 96°, about 97°, about 98°, about 99°, or about 100° with respect to the top surface of the vial stopper.

At 365, the infusion line spike is inserted through the vial stopper into the vial 300 at a point at which at least an end region of the infusion line spike is visible through the vial 300. For example, the infusion line spike is inserted through the vial stopper into the vial 300 until the infusion line spike is visible at a neck portion of the vial 300.

At 370, the process begins of moving the movable hanger portion 150 of the movable hanger label 100 from the first position (e.g., the closed position or the closed configuration) to the second position (e.g., the open position or the open configuration or the loop position or the loop configuration). In some examples, a first and/or second extended tab or corner or an end region of the movable hanger portion 150 may be lifted off or peeled away from the vial 300 and the remaining portion of the movable hanger label 100.

At 375, the process continues of moving the movable hanger portion 150 of the movable hanger label 100 from the first position to the second position. Consistent with implementations of the current subject matter, the movable hanger portion 150 is torn and/or peeled away from the movable hanger label 100 along the perforations 152, described above with reference to FIG. 1A-FIG. 2B.

At 380, when the movable hanger portion 150 is completely or near completely in the second position such that a loop is formed and able to be grasped, the vial 300 is inverted while holding in place in the vial the infusion line spike. At 385, the vial 300 is attached to an apparatus, such as an infusion stand, an infusion pole, or the like, by way of the movable hanger portion 150. In particular, with the movable hanger portion 150 in the open configuration, the vial 300 may be secured to an infusion stand, an infusion pole, or the like by the movable hanger portion 150 being looped or otherwise secured to an arm or extension of the infusion stand, the infusion pole, or the like. In this configuration, the vial 300 is supported by the movable hanger portion 150 of the movable hanger label 100 with the vial 300 oriented substantially downward.

Consistent with implementations of the current subject matter, the movable hanger portion 150 may support a weight of the vial 300 up to about 500 kg. The movable hanger portion 150 may support a weight of the vial 300 up to about 50 kg, about 100 kg, about 150 kg, about 200 kg, about 250 kg, about 300 kg, about 350 kg, about 400 kg, or about 450 kg. The movable hanger portion 150 may support a weight of the vial 300 up to about 10 kg, about 15 kg, about 20 kg, about 25 kg, about 30 kg, about 35 kg, about 40 kg, or about 45 kg. The movable hanger portion 150 may support a weight of the vial 300 up to about 1 kg, about 2 kg, about 3 kg, about 4 kg, about 5 kg, about 6 kg, about 7 kg, about 8 kg, or about 9 kg. The movable hanger portion 150 may support a weight of the vial 300 between about 0.5 kg and about 500 kg. The weight of the vial may be any value or subrange within the recited ranges, including endpoints.

In some implementations, the movable hanger portion 150 may be reinforced with extra, supportive material to resist breaking and to provide increased support for the vial 300. In some implementations, the movable hanger portion 150 may be made of a material that is stronger than the remainder of the movable hanger label 100.

The movable hanger label 100 and the movable hanger portion 150 may be of a variety of sizes and shapes, and are not limited to particular sizes and shapes. For example, an overall length of the movable hanger label 100 may be between about 75 mm and 100 mm, and an overall height of the movable hanger label 100 may be between about 30 mm and 40 mm. A width of a support portion (e.g., the portion from which the vial 300 is suspended when mounted or attached to an apparatus) of the movable hanger portion 150 may be between about 5.0 mm and about 7.0 mm; for example, about 5.0 mm, about 5.1 mm, about 5.2 mm, about 5.3 mm, about 5.4 mm, about 5.5 mm, about 5.6 mm, about 5.7 mm, about 5.8 mm, about 5.9 mm, about 6.0 mm, about 6.1 mm, about 6.2 mm, about 6.3 mm, about 6.4 mm, about 6.5 mm, about 6.6 mm, about 6.7 mm, about 6.8 mm, about 6.9 mm, or about 7.0 mm. A thickness of the hanger label may be between about 0.05 mm and about 0.25 mm; for example about 0.15 mm to about 0.18 mm. Any indicated parameter may be any value or subrange within the recited ranges, including endpoints.

The movable hanger label 100 and the movable hanger portion 150 are not limited to the sizes, shapes, and ratios shown in the example illustrations of FIG. 1A-FIG. 3B. Rather, the movable hanger label 100 and the movable hanger portion 150 consistent with implementations of the current subject matter may take the form of various sizes, shapes, and ratios. For example, the movable hanger label 100 and the movable hanger portion 150 may be sized and shaped to accommodate a variety of vials or containers.

As described herein, the movable hanger label 100 may be used to facilitate direct infusion of a drug contained in a vial to a patient. The drug contained in the vial is not, consistent with implementations of the current subject matter, diluted prior to administration. A process for administering the drug contained in the vial to the patient may include infusion of the drug to the patient with use of an infusion line and an infusion pump, followed by a saline flush also using the infusion line and the infusion pump. An infusion line spike may be positioned at a proximal end of the infusion line.

Figure 4:
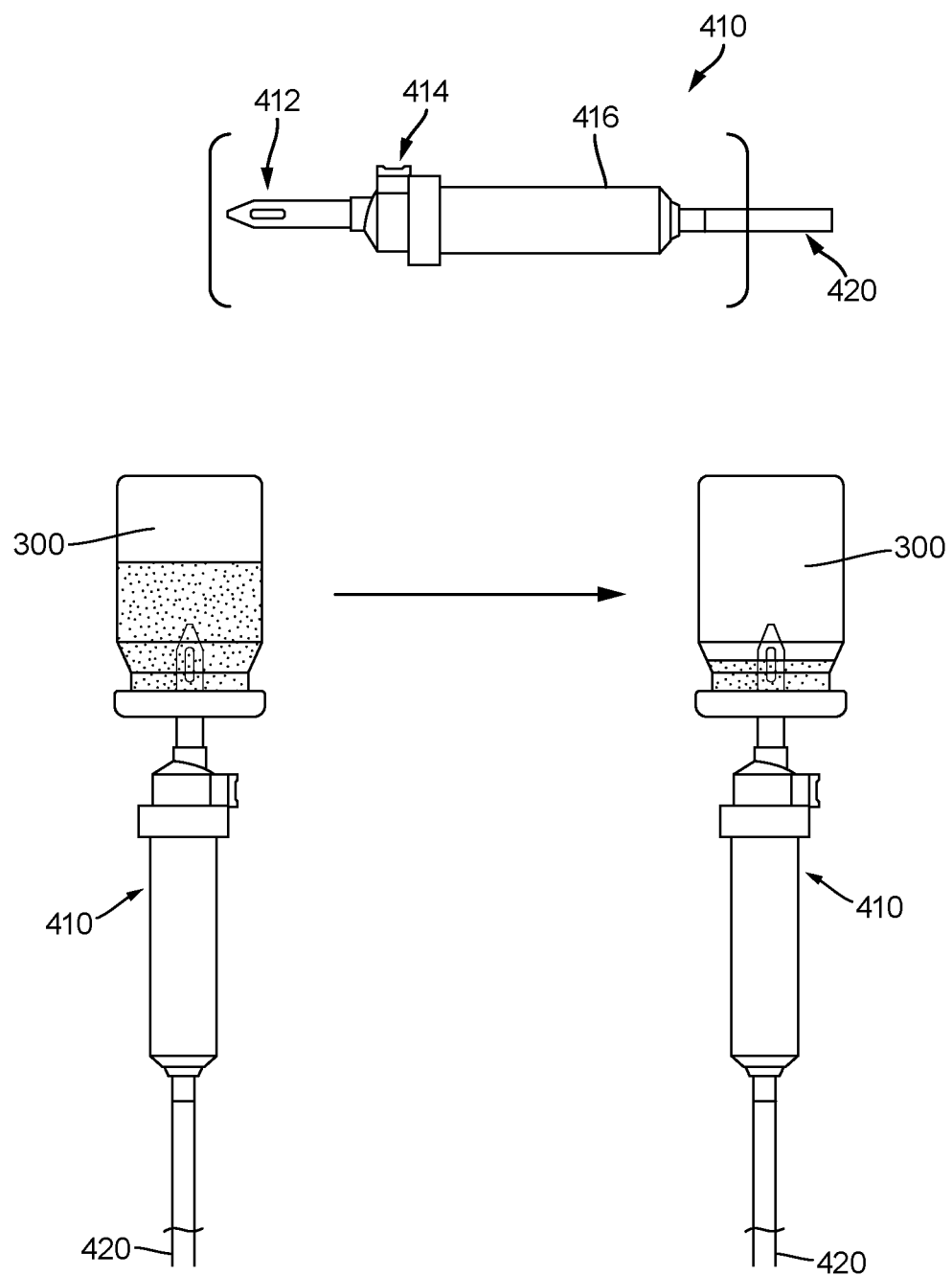
FIG. 4 is a diagram illustrating aspects of an infusion line spike for direct drug infusion in which the movable hanger label consistent with implementations of the current subject matter may be employed.

FIG. 4 is a diagram illustrating aspects of an example infusion line spike 410 for direct drug infusion that may be employed consistent with implementations of the current subject matter. As shown in FIG. 4, the infusion line spike 410 includes a drug port 412, an air venting cap 414, and a main body 416 in fluid communication with the drug port 412. The main body 416 interfaces with an infusion line 420 such that there is fluidic communication from the drug port 412, through the main body 416, to the infusion line 420. The infusion line spike 410 is configured to introduce the drug contained in the vial 300 into the infusion line 420, as illustrated in FIG. 4. Other mechanisms may be used in place of the infusion line spike configuration. The infusion line 420 interfaces with the infusion pump (not shown), which operates to pump the fluid or material contained in the infusion line 420 at a prescribed rate. At a distal end of the infusion line 420 is a needle (not shown) that is inserted into the patient for delivering the drug from the infusion line 420 to the patient.

Consistent with implementations of the current subject matter, the process for drug administration utilizing the movable hanger label 100 may include infusing the infusion line with a first quantity of saline. For example, the first quantity of saline may be provided in a saline bag or container (containing, for example, 0.9% NaCl), and the infusion line spike (or other mechanism) may interface with the saline bag or container to introduce (via the pump operation) the first quantity of saline into the infusion line. This may be done so that air is removed from the infusion line prior to the drug infusion into the patient (and prior to the needle insertion in the patient).

The process may continue by removing a vial cap from the vial containing the drug. In some examples, the vial may include a stopper at a top portion thereof, and the vial cap may be configured to cover the stopper. The stopper may be rubber or another resilient and compressible material to allow for the infusion line spike to pierce the stopper such that the infusion line spike is inserted into the vial, thereby allowing the drug contained in the vial to be directed to the infusion line.

The movable hanger label 100 adhered to the vial may then be opened such that the movable hanger portion 150 is moved from the first position (e.g., the closed configuration) to the second position (e.g., the open or loop configuration). As described herein, by moving the movable hanger portion 150 to the open or loop configuration, the vial is able to be attached to an apparatus to facilitate direct infusion of the drug from the vial. For example, the vial may hang via the movable hanger portion 150 from an infusion stand or the like.

Once the vial is properly positioned, the air venting cap on the infusion line spike may be opened, and the infusion pump may be set with an infusion rate and an infusion volume for the drug to be administered to the patient. When the infusion pump begins operating at the prescribed infusion rate, the drug travels from the vial, via the infusion line spike, through the infusion line to the needle inserted into the patient at the distal end of the infusion line.

V. Methods of Administration

In an aspect, a method of intravenously administering a drug to a patient is provided. The method may utilize a vial with a movable hanger label as described herein, or any other vial or container that may be suitable for this purpose.

The method includes administering the drug to the patient by intravenous administration, without diluting the drug prior to administration. In embodiments, the method also includes intravenously administering saline to the patient after the drug. This saline infusion can "flush" the infusion line and reduce the amount of drug left in the line after administration. For drugs administered in small volumes (e.g., less than or equal to about 60 mL, or less than or equal to about 40 mL), this step can allow administration of the full dose of drug to the patient. The method also can decrease the total time (drug administration plus saline flush) of administration to the patient compared to standard methods of administration.

The method may include infusing the infusion line with a first quantity of saline (or other appropriate liquid). For example, a first quantity of saline may be provided in a saline bag or container (containing, for example, 0.9% NaCl), and introduced (via the pump operation) into the infusion line. This may be done so that air is removed from the infusion line prior to the drug infusion into the patient (and prior to the needle insertion in the patient).

The drug may be administered using an infusion pump. Upon completion of the infusion volume of the drug being administered to the patient, a second drug may be administered to the patient following the same or similar procedure. The second drug may be of the same type or a different type as the drug that was first administered. Upon completion of the infusion volume of the drug being administered or following the administration of the second drug, the infusion line may be flushed with a second quantity of saline. For example, once the dose of the drug has been dispensed, the infusion line may be moved to a saline bag or container containing saline, for example 0.9% NaCl, for flushing the infusion line.

Consistent with implementations of the current subject matter, less than 1.5% of an initial volume of the drug may remain in the infusion line following the infusion of the second quantity of saline for an infusion time of up to about 30 minutes at an infusion rate of about 3 mL/min. The infusion time may include the drug administration time and the second saline flush time.

Consistent with implementations of the current subject matter, less than 5% of an initial volume of the drug may remain in the infusion line following the infusion of the second quantity of saline for an infusion time of up to about 10 minutes at an infusion rate of about 6 mL/min. Again, the infusion time may include the drug administration time and the second saline flush time. An initial amount of the drug in the vial may be less than about 30 mL.

A process for administering a drug to a patient, consistent with additional implementations of the current subject matter, may include infusing into the patient via an infusion line a first quantity of saline, followed by infusing into the patient via the infusion line an infusion volume of the drug from a vial for a first period of time. The drug may be administered at a fixed dose (e.g., the same dose regardless of the patient age and/or weight).

An initial amount of drug in the vial may be less than or equal to about 30 mL. In embodiments, the drug is not diluted prior to infusion into the patient. In some embodiments, the initial amount of drug in the vial is between about 1 mL and about 30 mL. In some embodiments, the initial amount of drug in the vial is between about 1 mL and about 20 mL. In some embodiments, the initial amount of drug in the vial is between about 1 mL and about 15 mL. In some embodiments, the initial amount of drug in the vial is between about 5 mL and about 30 mL. In some embodiments, the initial amount of drug in the vial is between about 10 mL and about 30 mL. In some embodiments, the initial amount of drug in the vial is between about 15 mL and about 30 mL. In some embodiments, the initial amount of drug in the vial is between about 5 mL and about 25 mL. In some embodiments, the initial amount of drug in the vial is between about 5 mL and about 20 mL. In some embodiments, the initial amount of drug in the vial is between about 5 mL and about 15 mL. The amount may be any value or subrange within the recited ranges, including endpoints.

In some embodiments, the initial amount of drug in the vial is less than or equal to about 30 mL, about 29 mL, about 28 mL, about 27 mL, about 26 mL, about 25 mL, about 24 mL, about 22 mL, or about 21 mL. In some embodiments, the initial amount of drug in the vial is less than or equal to about 20 mL. In some embodiments, the initial amount of drug in the vial is less than or equal to about 19 mL. In some embodiments, the initial amount of drug in the vial is less than or equal to about 18 mL. In some embodiments, the initial amount of drug in the vial is less than or equal to about 17 mL. In some embodiments, the initial amount of drug in the vial is less than or equal to about 16 mL. In some embodiments, the initial amount of drug in the vial is less than or equal to about 15 mL. In some embodiments, the initial amount of drug in the vial is less than or equal to about 14 mL. In some embodiments, the initial amount of drug in the vial is less than or equal to about 13 mL. In some embodiments, the initial amount of drug in the vial is less than or equal to about 12 mL. In some embodiments, the initial amount of drug in the vial is less than or equal to about 11 mL. In some instances, the initial amount of drug in the vial is less than or equal to about 10 mL. In some embodiments, the initial amount of drug in the vial is less than or equal to about 5 mL.

The patient may then be infused via the infusion line with a second quantity of saline for a second period of time. Consistent with implementations of the current subject matter, less than about 10% of the initial amount of the drug may remain in the infusion line after infusion of the second quantity of saline. In some embodiments, less than about 9%, 8%, 7%, or 6% of the initial amount of the drug may remain in the infusion line after infusion of the second quantity of saline. In some embodiments, less than about 5% of the initial amount of the drug may remain in the infusion line after infusion of the second quantity of saline. In some embodiments, less than about 4% of the initial amount of the drug may remain in the infusion line after infusion of the second quantity of saline. In some embodiments, less than about 3% of the initial amount of the drug may remain in the infusion line after infusion of the second quantity of saline. In some embodiments, less than about 2% of the initial amount of the drug may remain in the infusion line after infusion of the second quantity of saline. In other instances, less than about 1.5% of the initial amount of the drug may remain in the infusion line after infusion of the second quantity of saline. In some embodiments, less than about 1% of the initial amount of the drug may remain in the infusion line after infusion of the second quantity of saline.

In some embodiments, between about 0% and about 10% of the initial amount of the drug may remain in the infusion line after infusion of the second quantity of saline. In some embodiments, between about 0% and about 5% of the initial amount of the drug may remain in the infusion line after infusion of the second quantity of saline. In some embodiments, between about 0% and about 1.5% of the initial amount of the drug may remain in the infusion line after infusion of the second quantity of saline. In some embodiments, between about 1% and about 5% of the initial amount of the drug may remain in the infusion line after infusion of the second quantity of saline. In some embodiments, between about 1.5% and about 5% of the initial amount of the drug may remain in the infusion line after infusion of the second quantity of saline. The amount may be any value or subrange within the recited ranges, including endpoints.

The total of the first period of time (the time for the infusion of the drug) and the second period of time (the time for the saline flush) may be less than or equal to about 60 minutes, less than or equal to about 30 minutes, or less than or equal to about 15 minutes.

In embodiments, the total may be between about 5 min and about 60 min. In embodiments, the total may be between about 5 min and about 45 min. In embodiments, the total may be between about 10 min and about 45 min. In embodiments, the total may be between about 10 min and about 30 min. In embodiments, the total may be between about 15 min and about 30 min. In embodiments, the total may be between about 5 min and about 25 min. In embodiments, the total may be between about 5 min and about 20 min. The amount of time may be any value or subrange within the recited ranges, including endpoints.

The infusion volume of the drug may be between about 10 mL and about 30 mL, and the second quantity of saline may be between about 25 mL and about 90 mL.

In embodiments, the second quantity of saline may be between about 20 mL and about 100 mL. In embodiments, the second quantity of saline may be between about 25 mL and about 90 mL. In embodiments, the second quantity of saline may be between about 25 mL and about 80 mL. In embodiments, the second quantity of saline may be between about 25 mL and about 70 mL. In embodiments, the second quantity of saline may be between about 25 mL and about 60 mL. In embodiments, the second quantity of saline may be between about 25 mL and about 50 mL. In embodiments, the second quantity of saline may be between about 25 mL and about 40 mL. In embodiments, the second quantity of saline may be between about 25 mL and about 30 mL. The amount may be any value or subrange within the recited ranges, including endpoints.

The drug and/or second quantity of saline may be infused into the patient at an infusion rate between about 1 mL/min and about 10 mL/min. The drug and/or second quantity of saline may be infused into the patient at an infusion rate between about 2 mL/min and about 10 mL/min. The drug and/or second quantity of saline may be infused into the patient at an infusion rate between about 3 mL/min and about 10 mL/min. The drug and/or second quantity of saline may be infused into the patient at an infusion rate between about 1 mL/min and about 8 mL/min. The drug and/or second quantity of saline may be infused into the patient at an infusion rate between about 1 mL/min and about 6 mL/min. The drug and/or second quantity of saline may be infused into the patient at an infusion rate of about 1 mL/min. The drug and/or second quantity of saline may be infused into the patient at an infusion rate of about 2 mL/min. The drug and/or second quantity of saline may be infused into the patient at an infusion rate of about 3 mL/min. The drug and/or second quantity of saline may be infused into the patient at an infusion rate of about 4 mL/min. The drug and/or second quantity of saline may be infused into the patient at an infusion rate of about 5 mL/min. The drug and/or second quantity of saline may be infused into the patient at an infusion rate of about 6 mL/min. The drug and/or second quantity of saline may be infused into the patient at an infusion rate of about 7 mL/min. The drug and/or second quantity of saline may be infused into the patient at an infusion rate of about 8 mL/min. The drug and/or second quantity of saline may be infused into the patient at an infusion rate of about 9 mL/min. The drug and/or second quantity of saline may be infused into the patient at an infusion rate of about 10 mL/min. The amount may be any value or subrange within the recited ranges, including endpoints.

EXAMPLES

Example 1: Rapid and Ready-to-Infuse (RRTI) Atezolizumab

Simplifying dose preparation by allowing direct infusion of Tecentriq®, the cancer immunotherapy agent atezolizumab, and enabling rapid infusion (e.g., 10 minutes for IV infusion) can improve the experience of the healthcare professional and the patient experience.

The RRTI approach for IV infusion allows for administering medicine directly from the primary package (e.g., vial) which can simplify the healthcare professional's workflow. Infusing medicine rapidly (e.g., 10 min infusion time) can further improve patient experience. Therefore, Tecentriq® is a good candidate for RRTI as it is a liquid formulation (no reconstitution needed) and is provided as a flat dose.

The following protocol is an example method for rapid infusion of a liquid drug, e.g., atezolizumab, from a vial. First, prime the infusion line with normal saline (e.g., 0.9% NaCl) before insertion. Remove the vial cap and pierce the center of the rubber stopper with the infusion spike. FIG. 4 illustrates an infusion line spike alone (top) and after insertion into the vial (bottom). Ensure that the drug port section is resting in the neck region of the vial, near the stopper, as shown in the bottom of FIG. 4. Open the hanger label and hang the vial, inverted, on an IV stand. Open the air venting cap on the infusion line, and set infusion rate and volume to be infused (VTBI) per Table 1 and begin infusion. For example, for the 1680 mg dose, set VTBI to 14.0 mL and begin infusion. Once the infusion is complete, open another 15 cc vial and repeat the protocol. Set VTBI to 14.0 mL and begin infusion. Once the desired dose has been dispensed, move the infusion line to a container with 0.9% NaCl to flush the line, and set infusion rate and VTBI per Table 1.

Atezolizumab is available at three different doses (840 mg, 1200 mg, and 1680 mg), depending on the indication and protocol to be used. Currently, atezolizumab is diluted into a 250 mL infusion bag containing 0.9% Sodium Chloride Injection, USP prior to administration. The first infusion of atezolizumab is to be administered intravenously over 60 minutes. If the first infusion is tolerated, all subsequent infusions may be delivered over 30 minutes. TECENTRIQ® (atezolizumab) Prescribing Information, www.gene.com/download/pdf/tecentriq_prescribing.pdf.

A rapid and ready-to-infuse method for infusion of atezolizumab as described herein was tested. A total of six infusion scenarios were assessed. Two infusion times were assessed: 30 minutes for the initial dose, and 10 minutes for subsequent doses. Three doses were assessed: 840 mg, 1200 mg, and 1680 mg. To simplify the process for end users, it is proposed that the same infusion rate is used for all three tested doses under the same infusion time. In this assessment, a rate of 3 mL/min was tested for the 30 minute initial dose infusion, and a rate of 6 mL/min was tested for the 10 minute subsequent dose infusion. Table 1 provides the VTBI for the three doses and two infusion times.

TABLE 1

| | | Infusion Rates and Flushing Volumes | | | | | |
|---|---|---|---|---|---|---|---|
| | | Volume to be infused (VTBI) | | | | | |
| Total | | 840 mg | | 1200 mg | | 1680 mg | |
| infusion time | Infusion rate | Atezolizumab infusion | Saline flush | Atezolizumab infusion | Saline flush | Atezolizumab infusion | Saline flush |
| 30 min | 3 mL/min | 14.0 mL | 76.0 mL | 20.0 mL | 70.0 mL | 28.0 mL | 62.0 mL |
| 10 min | 6 mL/min | 14.0 mL | 46.0 mL | 20.0 mL | 40.0 mL | 28.0 mL | 32.0 mL |

Figure 5A:
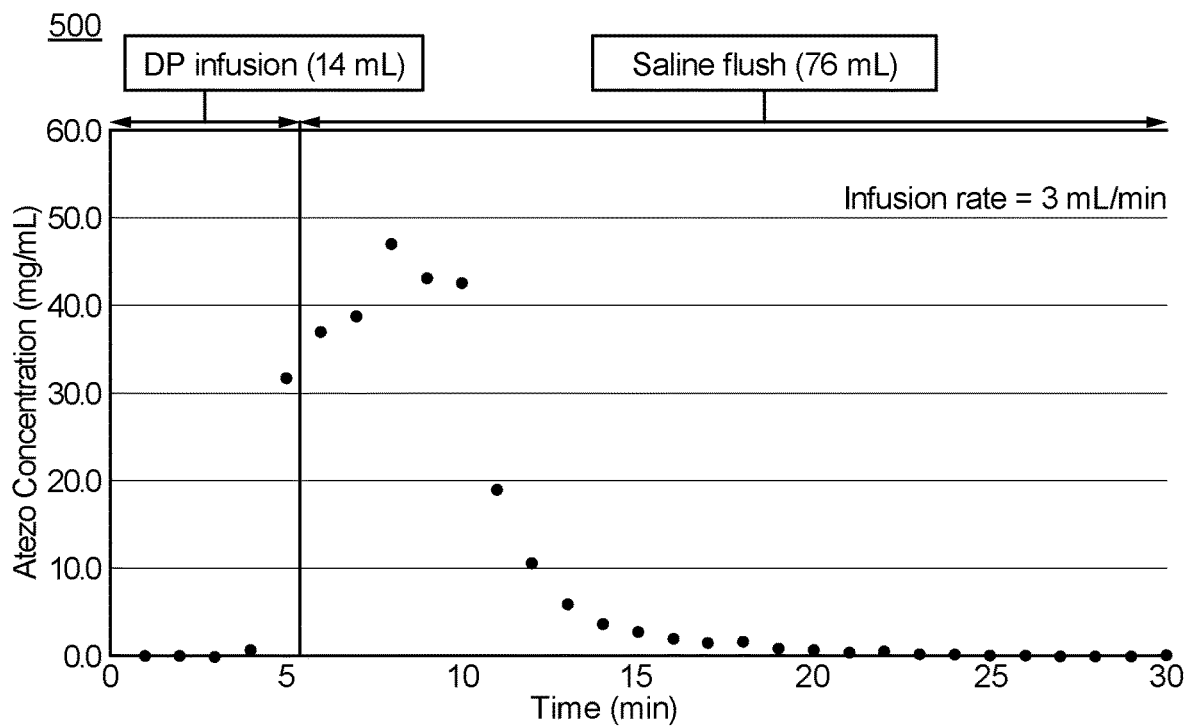
FIG. 5A is a graph of atezolizumab (atezo) concentration as a function of time for an 840 mg dose of atezolizumab infused over 30 minutes at an infusion rate of 3 milliliters per minute (mL/min) consistent with implementations of the current subject matter.
Figure 5B:
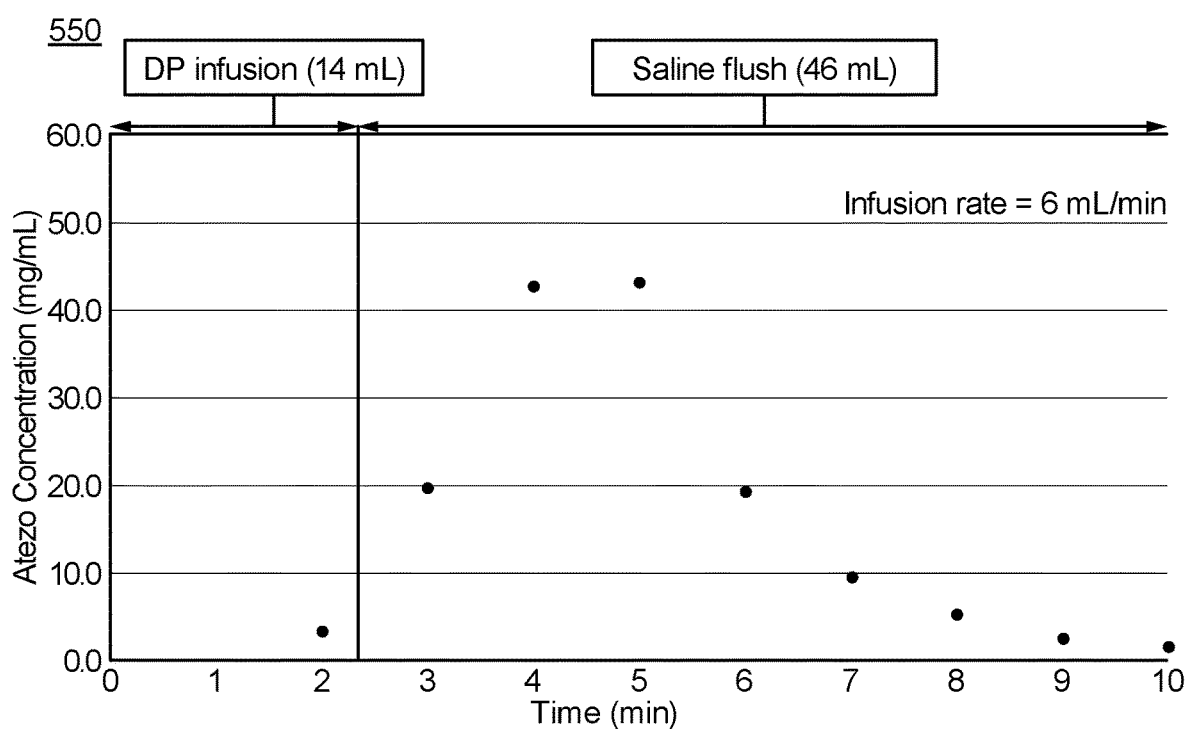
FIG. 5B is a graph of atezolizumab (atezo) concentration as a function of time for an 840 mg dose of atezolizumab infused over 10 minutes at an infusion rate of 6 mL/min consistent with implementations of the current subject matter.

FIG. 5A and FIG. 5B are graphs 500 and 550, respectively, of the atezolizumab concentration as a function of time for two scenarios. Scenario 1, shown in FIG. 5A, is an 840 mg dose of atezolizumab infused over 30 minutes. Scenario 2, shown in FIG. 5B, is an 840 mg dose of atezolizumab infused over 10 minutes. The atezolizumab concentration was measured from the end of the infusion line, which is the concentration that the patients are expected to experience.

Figure 6A:
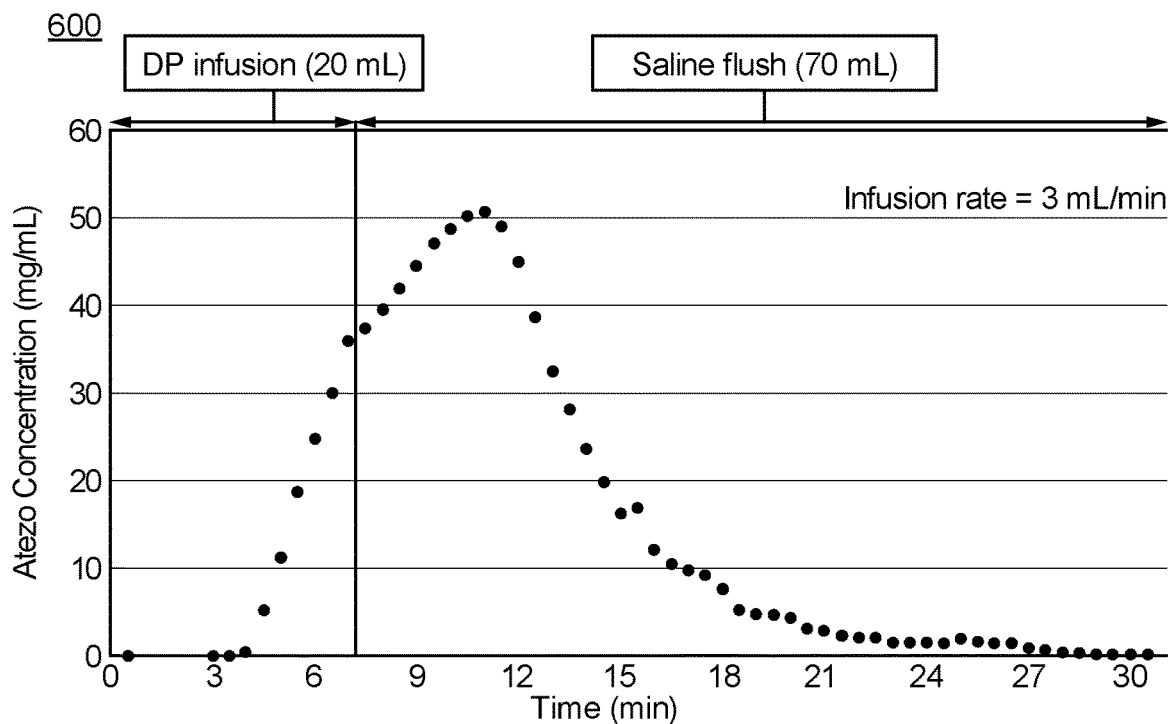
FIG. 6A is a graph of atezolizumab (atezo) concentration as a function of time for a 1200 mg dose of atezolizumab infused over 30 minutes at an infusion rate of 3 mL/min consistent with implementations of the current subject matter.
Figure 6B:
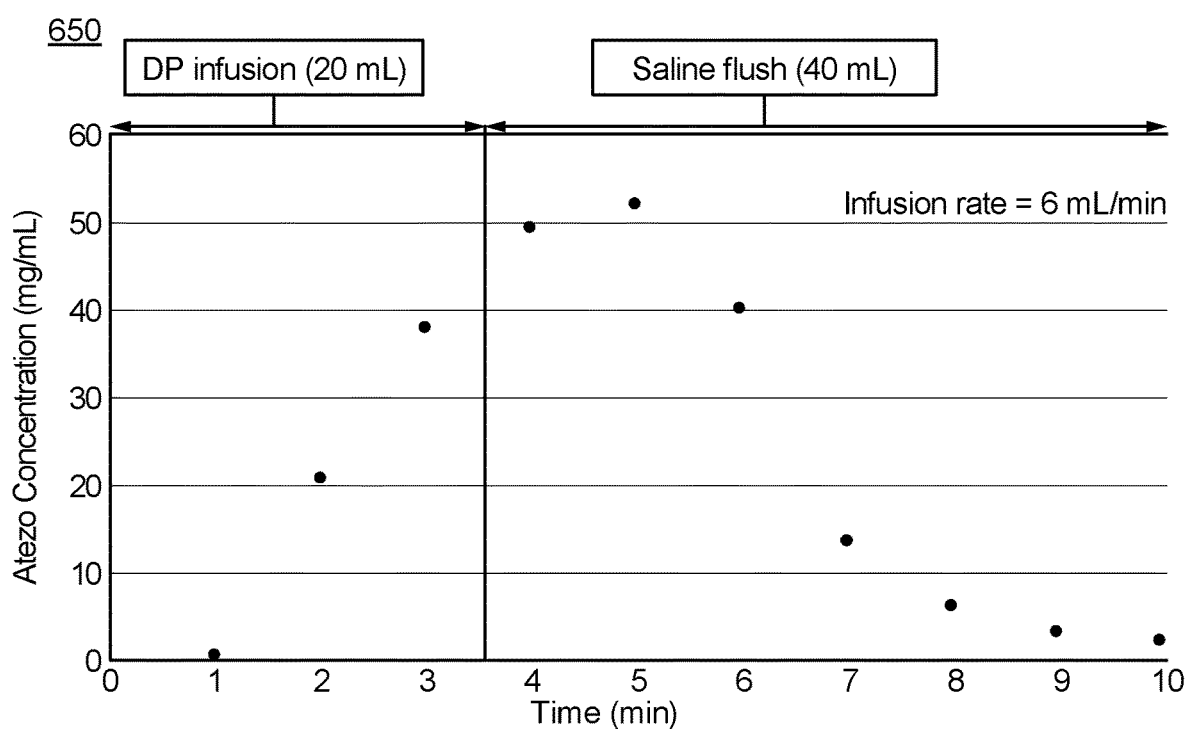
FIG. 6B is a graph of atezolizumab (atezo) concentration as a function of time for a 1200 mg dose of atezolizumab infused over 10 minutes at an infusion rate of 6 mL/min consistent with implementations of the current subject matter.

FIG. 6A and FIG. 6B are graphs 600 and 650, respectively, of the atezolizumab concentration as a function of time for two scenarios. Scenario 3, shown in FIG. 6A, is a 1200 mg dose of atezolizumab infused over 30 minutes. Scenario 4, shown in FIG. 6B, is a 1200 mg dose of atezolizumab infused over 10 minutes. The atezolizumab concentration was measured from the end of the infusion line, which is the concentration that the patients are expected to experience.

Figure 7A:
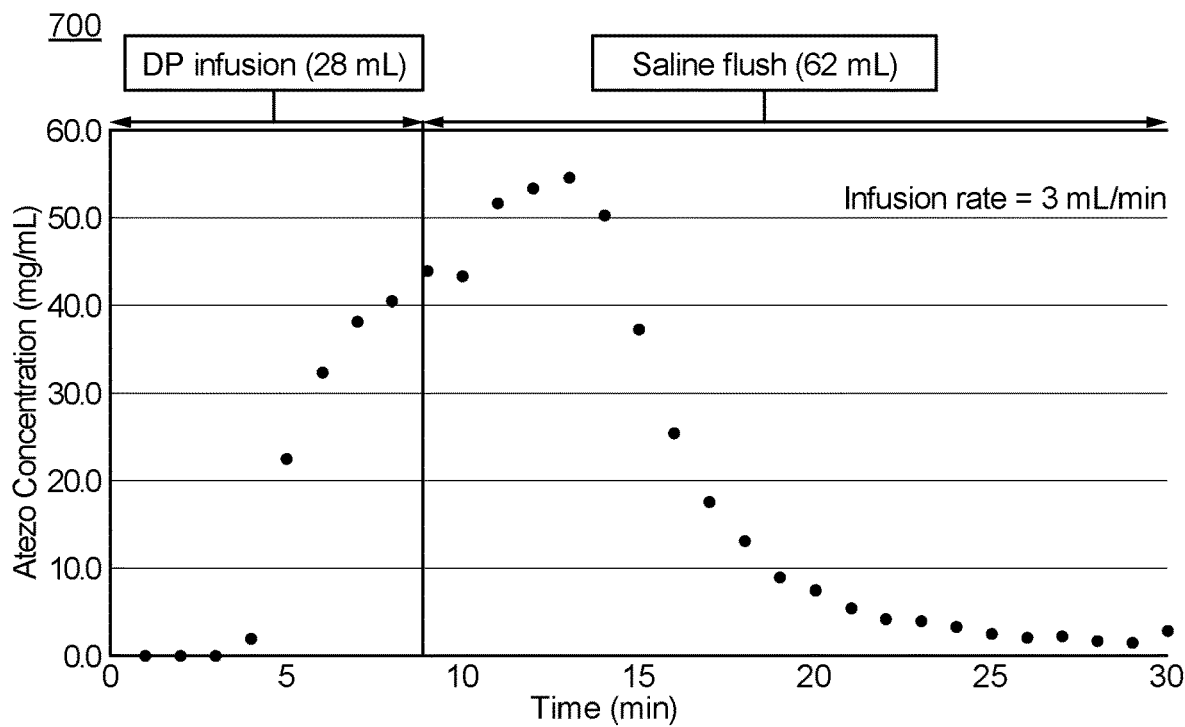
FIG. 7A is a graph of atezolizumab (atezo) concentration as a function of time for a 1680 mg dose of atezolizumab infused over 30 minutes at an infusion rate of 3 mL/min consistent with implementations of the current subject matter.
Figure 7B:
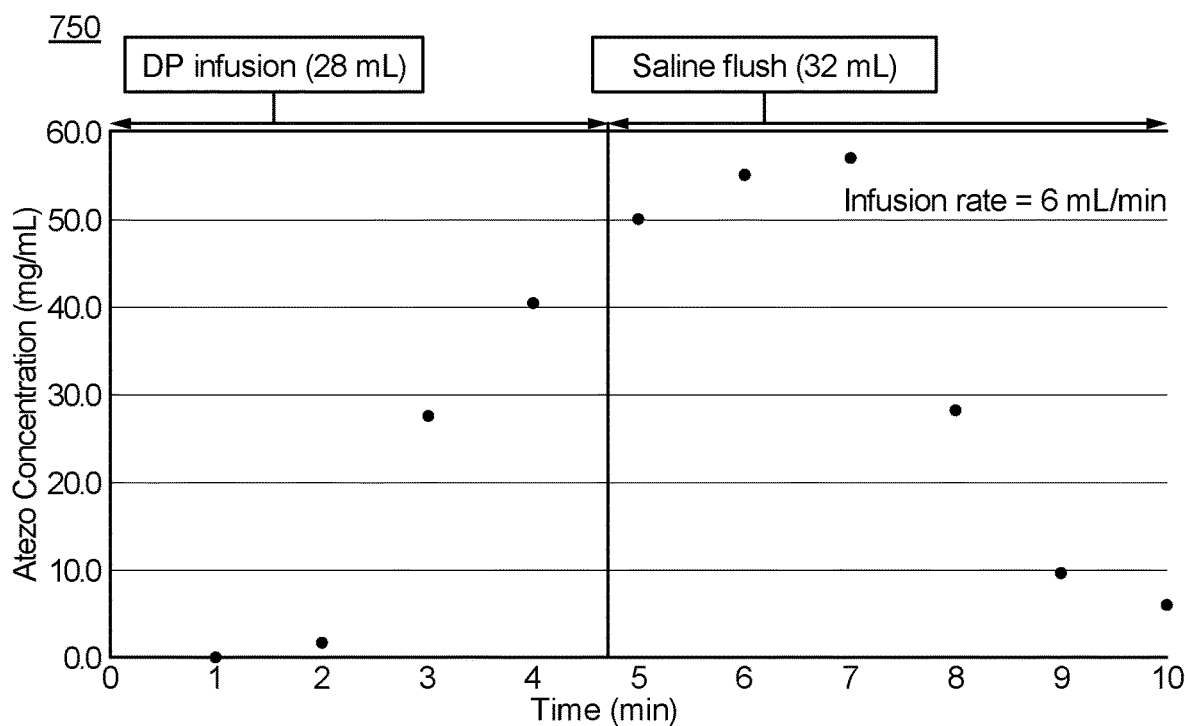
FIG. 7B is a graph of atezolizumab (atezo) concentration as a function of time for a 1680 mg dose of atezolizumab infused over 10 minutes at an infusion rate of 6 mL/min consistent with implementations of the current subject matter.

FIG. 7A and FIG. 7B are graphs 700 and 750, respectively, of the atezolizumab concentration as a function of time for two scenarios. Scenario 5, shown in FIG. 7A, is a 1680 mg dose of atezolizumab infused over 30 minutes. Scenario 6, shown in FIG. 7B, is a 1680 mg dose of atezolizumab infused over 10 minutes. The atezolizumab concentration was measured from the end of the infusion line, which is the concentration that the patients are expected to experience.

Table 2 below gives a summary of the six scenarios of simulated infusion and saline flush assessed. The maximum concentration (Cmax) of atezolizumab during infusion and saline flush was between 43.0 mg/mL and 57.1 mg/mL. The remaining atezolizumab in the infusion line after infusion (i.e., underdose) was 0.5% to 4.8%. The underdose due to remaining atezolizumab in the infusion line also applies to current IV bag set-ups, and is not a RRTI-specific risk.

TABLE 2

Summary of Simulated Infusion and Saline Flush

| Infusion time (min) | Dose (mg) | Vial size | Number of vials to be infused | Infusion rate (mL/min) | Flush volume (mL) | Approximate maximum atezolizumab concentration (mg/mL) | Atezolizumab concentration at the end of flushing (mg/mL) | Estimated leftover in the infusion line (i.e., underdose) |
|---|---|---|---|---|---|---|---|---|
| 30 | 840 | 15 cc | 1 | 3 | 76 | 43.0 | 0.2 | 0.5% |
| 30 | 1200 | 20 cc | 1 | 3 | 70 | 50.8 | 0.3 | 0.6% |
| 30 | 1680 | 15 cc | 2 | 3 | 62 | 54.6 | 0.8 | 1.2% |
| 10 | 840 | 15 cc | 1 | 6 | 46 | 43.2 | 0.9 | 2.5% |
| 10 | 1200 | 20 cc | 1 | 6 | 40 | 52.1 | 1.3 | 2.5% |
| 10 | 1680 | 15 cc | 2 | 6 | 32 | 57.1 | 3.5 | 4.8% |

Example 2: Load Testing

Load testing of the hanger label was performed based on or similar to DIN ISO 15137 (Self-adhesive hanging devices for infusion bottles and injection vials—Requirements and test methods; available on the ISO website, e.g. www.iso.org/standard/37391.html, and is incorporated herein by reference in its entirety). Permanent load test 24 h was performed based on/similar to DIN ISO 15137 with adapted weight of 500 g. Short-term load test 30 s based on/similar to DIN ISO 15137 with adapted weight of 1 kg. The hanger label meets or exceeds the requirements based on these tests.

Although the disclosure, including the figures, described herein may describe and/or exemplify different variations separately, it should be understood that all or some, or components of them, may be combined.

Although various illustrative embodiments are described above, any of a number of changes may be made to various embodiments. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the claims.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. References to a structure or feature that is disposed "adjacent" another feature may have portions that overlap or underlie the adjacent feature.

Terminology used herein is for the purpose of describing particular embodiments only and is not intended to be limiting. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as, for example, "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings provided herein.

Throughout this specification and the claims which follow, unless the context requires otherwise, the word "comprise", and variations such as "comprises" and "comprising" means various components can be co jointly employed in the methods and articles (e.g., compositions and apparatuses including device and methods). For example, the term "comprising" will be understood to imply the inclusion of any stated elements or steps but not the exclusion of any other elements or steps.

As used herein in the specification and claims, including as used in the examples and unless otherwise expressly specified, all numbers may be read as if prefaced by the word "about" or "approximately," even if the term does not expressly appear. The phrase "about" "or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. In embodiments, "about" refers to +/−10% or less of the stated value (or range of values). Any numerical values given herein should also be understood to include about or approximately that value, unless the context indicates otherwise.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, are possible.

In the descriptions above and in the claims, phrases such as, for example, "at least one of" or "one or more of" may occur followed by a conjunctive list of elements or features. The term "and/or" may also occur in a list of two or more elements or features. Unless otherwise implicitly or explicitly contradicted by the context in which it used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." Use of the term "based on," above and in the claims is intended to mean, "based at least in part on," such that an unrecited feature or element is also permissible.

The implementations set forth in the foregoing description do not represent all implementations consistent with the subject matter described herein. Instead, they are merely some examples consistent with aspects related to the described subject matter. Although a few variations have been described in detail herein, other modifications or additions are possible. In particular, further features and/or variations can be provided in addition to those set forth herein. For example, the implementations described above can be directed to various combinations and sub-combinations of the disclosed features and/or combinations and sub-combinations of one or more features further to those disclosed herein. In addition, the logic flows depicted in the accompanying figures and/or described herein do not necessarily require the particular order shown, or sequential order, to achieve desirable results. The scope of the following claims may include other implementations or embodiments.

What is claimed is:

1. A method, comprising:
    infusing, via an infusion pump, an infusion line with a first quantity of saline;
    removing a vial cap from a vial containing a drug, wherein the vial comprises a stopper at a top portion thereof, and further wherein the vial cap is configured to cover the stopper;
    piercing the stopper with an infusion line spike at a proximal end of the infusion line;
    opening, from a label adhered to the vial, a movable hanger into a loop configuration, wherein the movable hanger is formed from a portion of the label and is configured to move from a closed configuration into the loop configuration;
    hanging the vial, via the movable hanger, from an infusion stand; and
    opening an air venting cap on the infusion line spike.

2. The method of claim 1, further comprising:
    setting, on the infusion pump, an infusion rate and an infusion volume for the drug to be administered to a patient, wherein the drug travels from the vial, via the infusion line spike, through the infusion line to a needle inserted into the patient, wherein the needle is positioned at a distal end of the infusion line, and further wherein the infusion pump interfaces with the infusion line to pump the drug at the infusion rate.

3. The method of claim 2, further comprising:
    infusing, via the infusion pump and upon completion of administration of the drug to the patient, a second drug through the infusion line for administration to the patient, wherein the second drug is of a same type or a different type as the drug.

4. The method of claim 2, further comprising:
    infusing, via the infusion pump, the infusion line with a second quantity of saline.

5. The method of claim 4, wherein less than 1.5% of an initial volume of the drug remains in the infusion line following the infusion of the second quantity of saline for an infusion time of up to about 30 minutes at an infusion rate of about 3 mL/min, wherein the infusion time comprises a drug administration time and a second saline flush time.

6. An apparatus, comprising:
a label comprising:
- a back surface area configured to contact a vial;
- a front surface area opposite the back surface area; and
- a movable hanger traversing a portion of the back surface area of the label through a portion of the front surface area opposing the portion of the back surface area, the movable hanger configured to move from a first position to a second position; and
- wherein in the first position, the movable hanger is at least substantially aligned with a remainder portion of the back surface area and an opposing remainder portion of the front surface area, and
- wherein in the second position, the movable hanger is at least partially separated from the remainder portion of the back surface area and the opposing remainder portion of the front surface area, the label is adhered to the vial, and the movable hanger in the second position is configured to support a weight of the vial up to about 10 kg from an infusion stand.

7. The apparatus of claim 6, wherein the remainder portion of the back surface area of the label is configured to adhere to an outer sidewall of the vial.

8. The apparatus of claim 6, wherein the label comprises a flexible material.

9. The apparatus of claim 6, wherein the back surface area comprises the portion of the back surface area and the remainder portion of the back surface area, and wherein the front surface area comprises the opposing portion of the front surface area and the opposing remainder portion of the front surface area.

10. The apparatus of claim 6, wherein the label further comprises a perforation that extends through the back surface area and the front surface area, and further wherein the perforation defines at least a portion of a perimeter of the movable hanger.

11. The apparatus of claim 10, wherein the perforation is configured to cause the movable hanger to at least partially separate from the remainder portion of the back surface area and the opposing remainder portion of the front surface area.

12. The apparatus of claim 10, wherein the movable hanger is configured to move from the first position to the second position along the perforation.

13. The apparatus of claim 6, wherein the movable hanger in the second position comprises a loop configuration, the loop configuration comprising two fixed ends.

14. The apparatus of claim 6, wherein the movable hanger in the second position is positioned such that the vial hangs substantially downward away from the infusion stand.

15. The apparatus of claim 14, wherein the label comprises text on the front surface area, wherein the text is upside down, right side up, or a combination thereof when the vial hangs substantially downward.

16. The apparatus of claim 6, wherein a length of the label is between about 75 mm and about 100 mm.

17. The apparatus of claim 6, wherein a height of the label is between about 30 mm and about 40 mm.

18. The apparatus of claim 6, wherein a width of the movable hanger is between about 5 mm and about 7 mm.

* * * * *